United States Patent
Hoffmann et al.

(10) Patent No.: US 9,040,029 B2
(45) Date of Patent: May 26, 2015

(54) LEAVE-IN HAIR CONDITIONING COMPOSITION

(71) Applicant: KAO GERMANY GMBH, Darmstadt (DE)

(72) Inventors: Martin Hoffmann, Zwingenberg (DE); Magali Lateulere, Nyon (CH)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 13/963,354

(22) Filed: Aug. 9, 2013

(65) Prior Publication Data

US 2013/0330291 A1     Dec. 12, 2013

Related U.S. Application Data

(60) Division of application No. 12/941,263, filed on Nov. 8, 2010, now abandoned, which is a continuation-in-part of application No. 11/559,048, filed on Nov. 13, 2006, now abandoned.

(30) Foreign Application Priority Data

Nov. 16, 2005   (EP) .................................. 05024988

(51) Int. Cl.
| | | |
|---|---|---|
| *A61Q 5/12* | (2006.01) | |
| *A61K 8/891* | (2006.01) | |
| *A61K 8/37* | (2006.01) | |
| *A61K 8/58* | (2006.01) | |
| *A61K 8/33* | (2006.01) | |

(52) U.S. Cl.
CPC . *A61K 8/891* (2013.01); *A61K 8/37* (2013.01); *A61K 8/585* (2013.01); *A61K 2800/31* (2013.01); *A61Q 5/12* (2013.01); *A61K 8/33* (2013.01)

(58) Field of Classification Search
CPC ......... A61K 8/891; A61K 8/37; A61K 8/585; A61K 2800/01; A61K 8/33; A61Q 5/12
See application file for complete search history.

(56) References Cited

U.S. PATENT DOCUMENTS

| | | |
|---|---|---|
| 6,312,676 B1 | 11/2001 | Rechelbacher et al. |
| 2002/0122811 A1 | 9/2002 | Stein et al. |
| 2003/0118516 A1 | 6/2003 | Emmering et al. |

FOREIGN PATENT DOCUMENTS

| | | |
|---|---|---|
| EP | 1 192 934 A | 4/2003 |
| GB | 2 102 288 A | 2/1983 |
| WO | 97 47282 A | 12/1997 |

OTHER PUBLICATIONS

Dow Corning 345 Product Information, [online], Retrieved from URL: <www.dowcorning.com>, Retrieved [Aug. 27, 2008].
Pure Silicone Fluid, [online], Retrieved [Oct. 30, 2009], Retrieved from URL:<http://web.starlinx.com/www.clearcoproducts.com/standard_pure_silicones.html>.

*Primary Examiner* — Lezah Roberts
*Assistant Examiner* — Nannette Holloman
(74) *Attorney, Agent, or Firm* — Norris McLaughlin & Marcus PA

(57) ABSTRACT

Present invention relates to a non-aqueous leave-in conditioning composition for hair, especially for strongly damaged hair by chemical processes such as permanent shaping, oxidative coloration and bleaching. Accordingly, conditioning compositions of present invention comprise one or more cyclomethicone at a concentration of at least 50% by weight calculated to total composition, and at least one dialkyl carbonate.

13 Claims, No Drawings

LEAVE-IN HAIR CONDITIONING COMPOSITION

This application is a division of U.S. patent application Ser. No. 12/941,263, filed Nov. 8, 2010, which is, in turn, a continuation-in-part of U.S. patent application Ser. No. 11/559,048, filed Nov. 13, 2006, now abandoned, which, in turn, claims priority of European Patent Application No. 05 024 988.7, filed Nov. 16, 2005, the entire contents of which patent applications are hereby incorporated herein by reference.

Present invention relates to a non-aqueous leave-in conditioning composition for hair, especially for frizzy and/or strongly damaged hair by chemical processes such as permanent shaping, oxidative colouration and bleaching.

In quite large number of documents hair conditioning compositions have been disclosed. Those compositions are mainly of aqueous compositions and also mainly rinsed off after application and processing time.

Recently, leave-in conditioning compositions have become popular because of their easy, time saving and uncomplicated application. These compositions are not rinsed off from hair after application.

The purpose of application of conditioning preparation is as the name indicates to improve the surface properties of the hair fibres. For this purpose number of ingredients have been suggested in the literature. They vary from the ones with cationic charge to the oil or oily substances. Among the oil substances, silicone oils have increasingly been used in hair conditioning compositions. Although the state of the art quite advanced there is still need for further improvement.

It has surprisingly been found out that a water free composition comprising one or more cyclomethicone at a concentration of at least 50% by weight, calculated to total composition, and at least one dialkyl carbonate improves compatibility, elasticity and shine of hair and hair feels more natural upon touching.

Therefore the subject matter of the present invention is that a non-aqueous conditioning composition for hair comprising one or more cyclomethicone of the formula

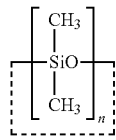

where n is a number between 3 and 7, at a concentration of at least 50% by weight, calculated to total composition, and at least one dialkyl carbonate of the formula

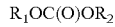

$R_1OC(O)OR_2$ where $R_1$ and $R_2$ are independent from each other linear or branched, saturated or unsaturated alkyl chains with 6 to 22 C atoms.

Concentration of cyclomethicone in the composition of the present invention is at least 50%, preferably between 55 and 90% and more preferably between 60 and 85% by weight, calculated to total composition. Suitable ones are commercially available from, for example, Dow Corning. The preferred ones are cyclomethicone available from Dow Corning under the trade names Dow Corning 1501, Dow Corning 244, 344 and 345 Fluid and cyclopentasiloxane, where n equals to 5 in the above given formula, available from Dow Corning under the trade name Dow Corning 245 Fluid.

Among dialkyl carbonates of the above formula, the most preferred ones are dicaprylyl carbonate known with the trade name Cetiol CC from Cognis and di(ethylhexyl) carbonate known with the trade name Tegosoft DEC from Degussa. Concentration of dialkylcarbonates in the compositions of the present invention varies between 0.1 to 20%, preferably 0.5 to 15% and more preferably 0.5 to 10% and most preferably 1 to 5% by weight, calculated to total composition.

Composition of the present invention preferably comprises in addition to cyclomethicone and dialkylcarbonate, at least one further silicone compound such as dimethicone and dimethiconol at a concentration of 0.1 to 20%, preferably 0.5 to 17.5% and more preferably 1 to 15% by weight, calculated to total composition. Suitable ones are commercially available for example from the company Dow Corning. The most preferred is dimethiconol.

Further, compositions of the present invention preferably comprise at least one arylated silicone such as phenyl trimethicone commercially available under the trade names such as Dow Corning 556 and Dow Corning 558. Among the arylated silicones the most preferred one is phenyl trimethicone. Arylated silicones should be included into the compositions at a concentration of 0.1 to 10%, preferably 0.1 to 7.5%, more preferably 0.2 to 5% and most preferably 0.5 to 5% by weight, calculated to the total composition.

Compositions of the present invention further optionally comprise at least one ester of aliphatic linear or branched saturated or unsaturated carboxylic acid with 12 to 22 carbon atoms with a primary or secondary linear or branched saturated or unsaturated alcohol with 3 to 18 C atoms at a concentration of 0.01 to 5%, preferably 0.05 to 4%, more preferably 0.1 to 2.5% by weight, calculated to total composition. Examples include isopropyl myristate, palmitate, stearate and isostearate, oleyl oleate, isocetyl stearate, hexyl laurate, dibutyl adipate, dioctyl adipate, myristyl myristate and oleyl erucate. The most preferred ones are isopropyl myristate, palmitate, stearate and isostearate.

Additionally, at least one natural oil may be incorporated into the compositions of the present invention. Suitable are such as olive oil, almond oil, avocado oil, weizenkeim oil, ricinus oil, jojba oil or their mixture. Concentration of these natural oil ingredients should be 0.01 to 2.5%, preferably 0.05 to 1.5%, more preferably 0.1 to 1% by weight, calculated to total composition.

The conditioner compositions may contain one or more organic solvent such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylene glycol, butylenes glycol, propylene glycol, benzyl glycol, ethylene glycol monoethylether, ethylene glycol monobutyl ether, ethylene glycol monophenyl ether, 1-phenylethylalcohol, 2-phenylethylalcohol, o-methoxyphenol, and their mixture. Concentration of organic solvents in the conditioner composition can be in the range from 0.1 to 20% by weight, preferably 0.5 to 17.5% by weight, and more preferably 1 to 15% by weight calculated to the total composition.

Compositions of the present invention preferably comprise at least one UV filter for protection of hair from environmental influences which may lead to loss of hair properties such as loss of elasticity, loss of hair colour (bleaching effect of sun light). Suitable UV-absorbing substances are such as ethyl hexyl methoxy cinnamate, octocrylene, 2,4-dihydroxybenzophenone, 2,2',4,4'-tetrahydroxy-benzophenone, 2-hydroxy-4-methoxybenzophenone, 2,2'-dihydroxy-4,4'-dimethoxybenzophenone, 2-hydroxy-5- chlorobenzophenone, 2,2'-dihydroxy-4-methoxybenzophenone, 2-hydroxy-4-octyloxybenzophenone, 2-hydroxy-4-methoxy-4'-methylbenzophenone, 3-benzyl-idenecampher, 3-(4'-methyl benzylidene)-DL-campher and their mixture. The preferred amount of the UV-absorber ranges from about 0.01% to 2.5%, more preferably from 0.05% to 1% by weight, calculated to the total composition.

Compositions of the present invention may certainly comprise fragrance and additional ingredients such as oil soluble dyes, vitamins, etc. compatible with the remaining part of the compositions which may be soluble or stably dispersable.

Compositions of the present invention are leave-in compositions and are applied to the hair and subsequently not rinsed off from hair. Accordingly, another subject of the present invention is process for conditioning hair wherein a composition comprising at least one cyclomethicone at a concentration of at least 50% by weight, calculated to total composition, and at least one dialkyl carbonate is applied onto either shampooed and towel dried hair or wet hair and homogeneously distributed and without rinsing off with water hair is dried. By the wet hair it is meant that shampooing hair is not a must and hair may easily be wetted by spraying water onto hair or by washing hair only with water and subsequently towel drying.

Compositions of the present invention can also be applied directly onto dry hair. Accordingly, further subject of the inventions is process for conditioning dry hair wherein a composition comprising at least one cyclomethicone at a concentration of at least 50% by weight, calculated to total composition, and at least one dialkyl carbonate is applied and homogeneously distributed.

Still further objective of the present invention is the use of the composition comprising at least one cyclomethicone at a concentration of at least 50% by weight, calculated to total composition, and at least one dialkyl carbonate for improving compatibility, elasticity, shine and natural feeling upon touching of hair, especially frizzy and/or strongly damaged hair.

The following examples are to illustrate the invention without limiting it.

EXAMPLE 1

|  | % by weight |
|---|---|
| Cyclomethicone | 83 |
| Phenyl trimethicone | 2 |
| Dimethiconol | 7.5 |
| Isopropyl myristate | 0.9 |
| Ethyl hexyl methoxycinnamate | 0.3 |
| Di(ethylhexyl) carbonate | 5 |
| Benzyl alcohol | 1.2 |
| Fragrance | 0.1 |

The above composition is prepared by combining together all ingredients one by one.

The above composition was applied to a shampooed and towel dried hair. It was found out that hair has excellent compatibility, elasticity and shine in addition to extreme natural feeling upon touching. The exclusion of di(ethylhexyl) carbonate resulted in loss of elasticity and hair thus obtained felt less natural.

Similar results were obtained with the examples below.

EXAMPLE 2

|  | % by weight |
|---|---|
| Cyclopentasiloxane | 80 |
| Phenyl trimethicone | 2 |
| Dimethiconol | 10 |
| Isopropyl palmitate | 1 |
| Ethyl hexyl methoxycinnamate | 0.5 |
| Di(ethylhexyl) carbonate | 4 |
| Ethanol | 2.4 |
| Fragrance | 0.1 |

EXAMPLE 3

|  | % by weight |
|---|---|
| Cyclopentasiloxane | 70 |
| Phenyl trimethicone | 1.5 |
| Dimethiconol | 11 |
| Isopropyl palmitate | 1.5 |
| Benzophenone-3 | 0.3 |
| Di(ethylhexyl) carbonate | 3 |
| Ethanol | 12.4 |
| Jojoba oil | 0.2 |
| Fragrance | 0.1 |

EXAMPLE 4

|  | % by weight |
|---|---|
| Cyclopentasiloxane | 70 |
| Phenyl trimethicone | 1.1 |
| Dimethiconol | 10 |
| Isopropyl stearate | 0.5 |
| Octocrylene | 0.5 |
| Di(ethylhexyl) carbonate | 3 |
| Ethanol | 14.4 |
| Almond oil | 0.4 |
| Fragrance | 0.1 |

The invention claimed is:
1. A method for improving elasticity of hair, the method comprising
applying a composition to the hair thereby increasing the elasticity of the hair, wherein the composition comprises a single-phase, transparent, non-aerosol, non-aqueous composition comprising one or more cyclomethicone of the formula

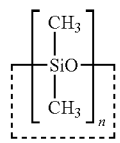

where n is a number between 3 and 7, at a concentration of between 55 to 90% by weight, calculated to the total composition, and at least one dialkyl carbonate of the formula $R_1OC(O)OR_2$ where R1 and R2 are independent from each other linear or branched saturated or unsaturated alkyl chains with 6 to 22 C atoms, wherein the at least one dialkyl carbonate is present at a concentration between 0.1 and 20% by weight, calculated to the total composition.

2. The method according to claim 1 wherein the one or more cyclomethicone is present at a concentration of between 60% to 85% by weight, calculated to the total composition.

3. The method according to claim 2 wherein the cyclomethicone is present at a concentration of between 70% to 80% by weight, calculated to the total composition.

4. The method according to claim 1 further comprising at least one further silicone compound selected from dimethicone and dimethiconol at a concentration of 0.1 to 20% by weight, calculated to the total composition.

5. The method according to claim 1 further comprising at least one arylated silicone at a concentration of 0.1 to 10% by weight, calculated to the total composition.

6. The method according to claim 1 further comprising at least one ester of aliphatic or branched, saturated or unsaturated carboxylic acid with 12 to 22 carbon atoms with a primary or secondary linear or branched saturated or unsaturated alcohol with 3 to 18 carbon atoms at a concentration of 0.1 to 5% by weight, calculated to the total composition.

7. The method according to claim 1 further comprising at least one natural oil.

8. The method according to claim 1 further comprising at least one at least one organic solvent.

9. A method for improving elasticity of hair, the method comprising:

applying a single-phase, transparent, non-aerosol, non-aqueous composition to the hair thereby increasing elasticity of the hair, wherein the composition comprises one or more cyclomethicone of the formula

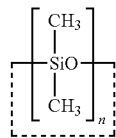

where n is a number between 3 and 7, at least one dialkyl carbonate comprising at least one of dicaprylyl carbonate and di(ethylhexyl) carbonate, at least one further silicone compound comprising at least one of dimethicone and dimethiconol, at least one arylated silicone, and at least one ester of carboxylic acid selected from the group consisting of isopropyl myristate, isopropyl palmitate, isopropyl stearate, isopropyl isostearate, oleyl oleate, isocetyl stearate, hexyl laurate, dibutyl adipate, dioctyl adipate, myristyl myristate and oleyl erucate.

10. The method according to claim 9, wherein the one or more cyclomethicone is cyclopentasiloxane.

11. The method according to claim 9, wherein the at least one arylated silicone is phenyl trimethicone.

12. The method according to claim 9, wherein the at least one ester of carboxylic acid is selected from the group consisting of isopropyl myristate, isopropyl palmitate, isopropyl stearate, isopropyl isostearate.

13. The method according to claim 9, wherein the composition further comprises at least one UV-absorbing substance selected from the group consisting of ethyl hexyl methoxy cinnamate, octocrylene, 2,4-dihydroxybenzophenone, 2,2',4, 4'-tetrahydroxy-benzophenone, 2-hydroxy-4-methoxybenzophenone, 2,2'-dihydroxy-4,4'-dimethoxybenzophenone, 2-hydroxy-5-chlorobenzophenone, 2,2'-dihydroxy-4-methoxybenzophenone, 2-hydroxy-4-octyloxybenzophenone, 2-hydroxy-4-methoxy-4'-methylbenzophenone, 3-benzylidenecampher, 3-(4'-methyl benzylidene)-DL-campher and their mixtures.

\* \* \* \* \*